United States Patent
Takaishi et al.

[11] 3,976,712
[45] Aug. 24, 1976

[54] 2,4-EXO-ETHANOBICYCLO [3.3.1]NONANE

[75] Inventors: Naotake Takaishi, Iwademachi; Yoshiaki Inamoto, Wakayama; Kiyoshi Tsuchihashi, Kainan, all of Japan

[73] Assignee: Kao Soap Co., Ltd., Tokyo, Japan

[22] Filed: July 17, 1975

[21] Appl. No.: 596,618

[30] Foreign Application Priority Data
July 24, 1974  Japan .................................. 49-84944

[52] U.S. Cl. ...................... 260/666 PY; 260/666 M
[51] Int. Cl.² ......................................... C07C 13/28
[58] Field of Search ................... 260/666 PY, 666 M

[56] References Cited
OTHER PUBLICATIONS
David P. G. Hamon et al., *J. Org. Chem.*, vol. 39, No. 18, 2803–2804, 1974.
Naotake Takaishi et al., *J. Org. Chem.*, vol. 40, No. 3, 276–281, 1975.

*Primary Examiner*—Veronica O'Keefe
*Attorney, Agent, or Firm*—Woodhams, Blanchard and Flynn

[57] ABSTRACT

2,4-exo-ethanobicyclo[3.3.1]nonane having the formula (I):

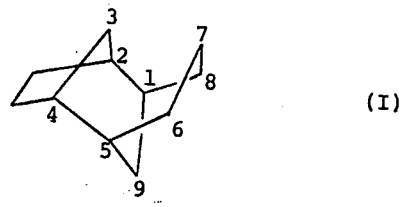

(I)

is prepared by treating 2-endo-hydroxymethyl-2,3-exo-trimethylenenorbornane having the formula (II):

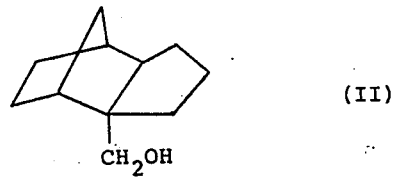

(II)

with a hydride donor and an acid catalyst.

1 Claim, No Drawings

2,4-EXO-ETHANOBICYCLO (3,3.1)NONANE

BACKGROUND OF THE INVENTION

1. FIELD OF THE INVENTION

This invention relates to a tricycloundecane having the formula (I) given below, namely, 2,4-exo-ethanobicyclo[3.3.1]nonane, and a process for preparing same. More particularly, this invention relates to a process in which a compound having the formula (II) given below, namely, 2-endo-hydroxymethyl-2,3-exo-trimethylenenorbornane, is reacted with a hydride donor in the presence of an acid catalyst thereby to cause simultaneously the skeletal rearrangement and hydride transfer reduction, whereby 2,4-exo-ethanobicyclo[3.3.1]nonane (tricyclo[4.3.1.1$^{2,4}$]undecane) is obtained. This reaction is represented by the following reaction scheme:

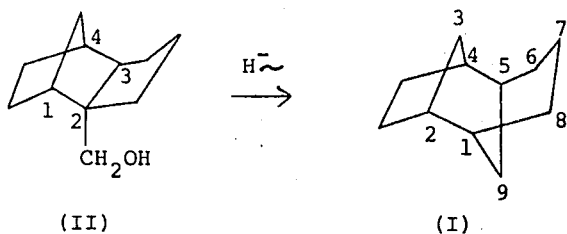

2,4-exo-ethanobicyclo[3.3.1]nonane (I) obtained according to the process of this invention is a novel tricyclic hydrocarbon. It can be converted through bromination and ritter reaction into a usful antivalal agent, 2,4-ethanobicyclo[3.3.1]nonylamine. In view of its molecular structure, this compound also possesses the same utilities as those of adamantane, that is, it is useful as a modifier moiety of various pharmaceutical compounds, an additive to lubricating oils, an extreme pressure lubricant, an antirust agent and an oiling agent for fibers, and as an intermediate for synthesizing other known, useful compounds. See the section entitled "Adamantane" in the Supplement Volume of Kirk-Othmer's *Encyclopedia of Chemical Technology*.

We have studied the hydride transfer reduction and rearrangement of various triicycloalkanols. We found that 2-endo-hydroxymethyl-2,3-exo-trimethylenenorbornane having the above formula (II) and its epimer having the following formula (IIa):

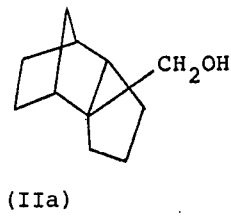

namely, 2-exo-hydroxymethyl-2,3-endo-trimethylenenorbornane, have quite different reactivities. More specifically, the compound (II) gives the compound (I) in as high a selectivity as 93% by the reaction in the presence of a hydride donor and an acid catalyst, whereas in the case of the compound (IIa) isomerization of the skeleton is not effected at all and the hydroxymethyl group is reduced to a methyl group. We have made various examinations of reaction conditions based on this discovery and as a result, we have now completed this invention.

More specifically, the essence of this invention lies in that the starting substance (II) rearranges in the presence of an acid catalyst and a hydride donor thereby to cause simultaneously isomerization of the skeleton of the compound (II) and reduction of the rearranged tricyclic carbocation to the corresponding tricycloundecane. The process of this invention can be practiced very easily and the object of this invention can be attained by mixing and reacting the starting substance (II), the hydride donor and the acid catalyst.

Any substances that are stable to the acid catalyst to effect the rearrangement of the carbinol (II), and at the same time give off hydride relatively easily can be used as the hydride donor in the process of this invention. As typical examples of such a substance, there can be mentioned alkanes containing no tertiary hydrogen atoms, such as n-alkanes having 4 to 10 carbon atoms, e.g., n-butane, n-pentane, n-hexane, n-heptane and n-octane, and cycloalkanes having 5 to 10 carbon atoms, e.g., cyclopentane, cyclohexane, cycloheptane and cyclooctane.

Various Lewis acids and Bronsted acids are effectively used as the acid catalyst in this invention. As the Lewis acid, there can be mentioned, for example, aluminum halides such as aluminum chloride and aluminum bromide, zinc halides such as zinc chloride an zinc bromide, boron halides such as boron trifluoride, and antimony halides such as antimony pentafluoride and antimony pentachloride. As the Bronsted acid, there can be mentioned, for example, sulfuric acid, fluorosulfonic acid, chlorosulfonic acid, methanesulfonic acid, benzenesulfonic acid and p-toluenesulfonic acid.

The amount used of the catalyst, per mole of the starting substance (II), is preferably 1 to 10 moles in the case of a Lewis acid and 2 to 500 moles in the case of a Bronsted acid. The amount of the hydride donor is not particularly critical, but it is preferred that it is used in an amount of 5 to 1000 times the weight of the starting substance (II).

The reaction temperature is −50° to +100°C, preferably −30° to +80°C. At a temperature lower than 50°C, the intended reaction hardly occurs, and at a temperature higher than +100°C, formation of tarry materials predominates.

That the product obtained by the process of this invention has the structure of 2,4-exo-ethanobicyclo[3.3.1]nonane shown by the above formula (I) is demonstrated by the following.

According to the carbon-13 nuclear magnetic spectroscopy including off-resonance proton decoupling technique, it was found that the molecule consists of seven different kinds of carbon atoms. As is shown by the spectral intensity proportional to the number of $^{13}$C nuclei and fine structure of the signals on off-resonance proton decoupling, the molecule was indicated to contain three single intensity methylene groups, two double intensity methylene groups, and two double intensity methine grous. Examination of a Dreiding molecular model shows that the number of all the possible tricycloundecane isomers that do not contain any three and four-membered rings amounts to seventy (Cf. N. Takaishi, Y. Inamoto, and K. Aigami, *J. Org. Chem.*, 40,276 (1975), of which only four compounds correspond to the observed spectrum. These four isomers are the compound (I), the endo isomer of the compound (I) having the formula (Ia):

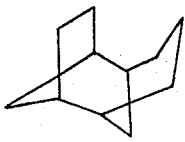

(Ia)

and exo- and endo isomers of 6,7-trimethylenebicyclo[3.2.1] octane having the formulae (III) and (IIIa):

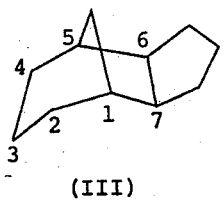      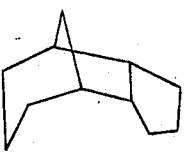

(III)                    (IIIa)

Compounds (III) and (IIIa) are also novel compounds which were first synthesized by us (Takaishi, Inamoto and Tsuchihashi, Japanese patent application Ser. No. 63236/74, filed June 4, 1974, corresponding to U.S. Ser. No. 582,108 filed May 30, 1975, entitled *Process for the Preparation of Tricyclo-[5.3.1.0³,⁸]undecane*, the entire contents of which are incorporated herein by reference). The physical properties and various spectra of the product obtained according to the process of this invention are not in agreement with those of (III) and (IIIa). Thus, the product of the present invention was shown not to be 6,7-trimethylenebicyclo[3.2.1]octanes.

The fact that the product of this invention is not of the structure (Ia) can be indirectly proved by the mechanism of formation of the product from (II) according to the process of this invention and the difference in the molecular stability of (I) and (Ia).

Norborn-2-endo-ylcarbinyl cation (IV) formed in the Demjanov rearrangement and solvolysis is isomerized with a high selectivity to bicyclo[3.2.1]oct-2-yl cation (V) as shown below:

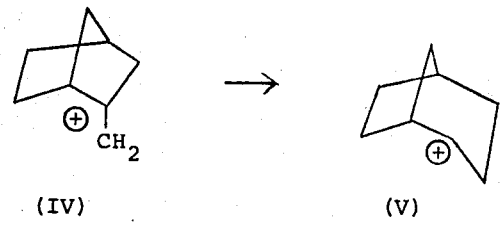

(IV)                    (V)

In contrast, it is well known that the exo-carbinyl cation (IVa), which is an epimer of (IV)), gives various products such as (V), (VI) and (VIII) as shown below:

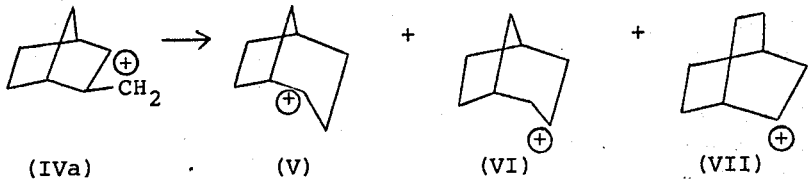

(IVa)      (V)      (VI)      (VII)

(C. D. Gutsche and D. Redmore, Carbocyclic Ring Expansion Reactions, page 3 (1968), Academic Press Inc., New York, N.Y.,; J. A. Berson and R. Reynolds Warnhoff, *J. Amer. Chem. Soc.*, 84, 682 (1962); M. A. Mckinney and P. P. Patal, *J. Org. Chem.*, 38 4059 (1973); R. R. Sauers and R. T. Tucker, ibid., 28, 876 (1963); and P. K. Freeman and K. B. Desai, ibid., 36, 1554 (1971). Since it can be considered that (IV) is included in (II) as a partial structure of (II), it is highly probable that (II) gives selectively (I). As a simplest course for (II) to give (Ia), there may be considered a reaction course in which (II) is first subjected to Wagner-Meerwein rearrangement to form (IIa) (or a corresponding carbinyl cation) and this then undergoes ring expansion. However, this reaction pathway is excluded for the following two reasons. In general, an exo isomer is theremodynamically more stable than an endo isomer. Assuming the same relative stability for II and IIa, it is reasonable to infer that (II) is more stable than (IIa). It can hardly be considered that stable (II) would be isomerized to unstable (IIa) under the reaction conditions adopted in this invention, where thermodynamic control of the reaction prevails (N. Takaishi, Y. Inamoto and K. Aigami, *Loc. Cit.*). Even if (II) was isomerized to (IIa), it is clearly deomonstrated in our experiments that (IIa) is not converted to (Ia) but the hydroxymethyl group is reduced to a methyl group to give 2-exo-methyl-2,3-endo-trimethylenenorbornane. From the foregoing two reasons, there is no possibility that the reaction pathway of (II) → (IIa) → (Ia) might occur.

The possibility of formation of (Ia) from (II) through a complicated adamantane rearrangement reaction with the intermediacy of various carbocations, not through a simple pathway (II) → (IIa), will now be examined. It is concluded that there can hardly be such a possibility. It was proved that the proportion of various products obtained by the adamantane rearrangement is determined by the relative thermodynamic stabilities of the products. As described below, it is considered that (I) is by about 10 Kcal/mole more stable than (Ia). Although no data has been reported about the thermodynamic stabilities of (I) and (Ia), the difference in the stability of the hypothetical tricyclodecanes having the formulas (VIII) and (VIIIa), and which are the adjacent lower homologs of (I) and (Ia), has been calculated with molecular mechanics.

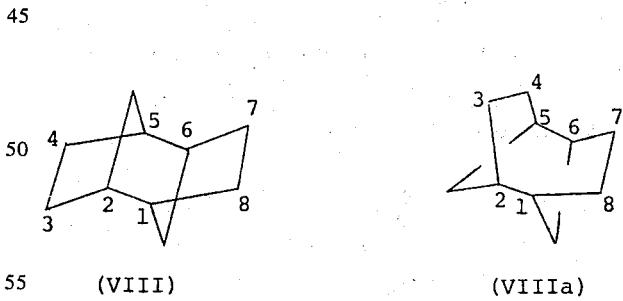

(VIII)                  (VIIIa)

According to the calculation, exo structure (VIII) is more stable than the endo structure (VIIIa) by 9.7 Kcal/mole, (Schleyer et al., *J. Amer. Chem. Soc.*, 95,5679 (1973). If one $CH_2$ group is added to the 1-8-7-6 bridge of (VIII) and (VIIIa), (I) and (Ia) are obtained, respectively. Since this increase of the CH$_2$ group is effected at a position that is not important for establishing the molecular energy of (VIII) or (VIIIa), it is expected that the difference in the relative stability between (VIII) and (VIIIa) is hardly changed by this increase of one CH$_2$ group. From these facts, it can be inferred that (I) is more stable than (Ia).

All the foregoing considerations made from the viewpoint of the reaction mechanism and the stability of the product support the conclusion that the product obtained according to the process of this invention has the structure shown by the formula (I).

The starting substance (II) used in this invention is a novel compound, which can be synthesized, for example, by the following method (Takaishi, Inamoto and Tsuchihashi, Japanese patent application Ser. No. 72523/73, corresponding to U.S. Ser. No. 482,434, filed June 24, 1974, the entire contents of which are incorporated herein by reference).

According to the process of Koch et al. (*Liebigs Ann. Chem.*, 638, 111 (1960), 2-exo-hydroxy-5, 6-exo-trimethylenenorbornane is converted to a mixture of epimers of 2-carboxy-2,3-trimethylenenorbornane. The mixture is esterified and the mixture of the esters is fractionated by distillation, chromatography or any other conventional method to separate the respective epimers. Each epimer thus obtained is reduced by lithium aluminum hydride to give (II) and (IIa), respectively.

This invention will now be described in more detail by reference to the following illustrative Examples. Further, the synthesis of the starting substance (II), its epimer (IIa) and a standard substance of the reaction product of (IIa), i.e., 2-exo-methyl-2,3-endo-trimethylenenorborane, will also be described by reference to Preparations.

PREPARATION 1

This Preparation describes the synthesis of 2-carboxy-2,2-trimethylenenorbornane by the Koch reaction.

A 2-liter, 4-neck, round-bottom flask was charged with 1178 g of concentrated sulfuric acid, and a solution of 114 g (0.75 mole) of 2-exo-hydroxy-5,6-exo-trimethylenenorbornane dissolved in 150 ml of n-hexane and 207 g of formic acid was added dropwise to the charge in the flask over a period of 1.5 hours while maintaining the inside temperature of the flask at 10 to 14°C.

The mixture was stirred at the same temperature for 1 hour, and then the reaction mixture was poured onto 3 Kg of ice. The precipitated crystals and the organic layer were extracted 2 times with 1 l of diethyl either, and the extract was washed with water and extracted 3 times with a 5% aqueous solution of caustic soda. The alkaline solution was made strongly acidic by 37% hydrochloric acid, and the resulting precipitate was separated by filtration, washed with water and air-dried to obtain 91 g (yield = 67%) composed of 62% (gas chromatogram area %) of 2-endo-carboxy-2,3-exo-trimethylenenorbornane having a melting point of 113° to 115°C (112° to 113°C as taught in the above-mentioned reference of Koch et al.) and 38% (gas chromatogram area %) of 2-exo-carboxy-2,3-endo-trimethylenenorborane having a melting point of 95° to 96°C (97° to 98°C as taught in the above-mentioned reference of Koch et al.). Each compound was separated and confirmed by gas chromatography (silicone SE-30; column temperature = 170°C).

Elementary Analysis Values as $C_{11}H_{16}O_2$: Found: C, 73.3; H, 8.9. Calculated: C, 73.30; H, 8.95%.

PREPARATION 2

This Preparation describes the esterification of 2-carboxy-2,3-trimethylenenorbornane.

In a round-bottom flask having a capacity of 500 ml, 88 g (0.49 mole) of the carboxylic acid obtained in Preparation 1 was mixed with 119 g (1 mole) of thionyl chloride, and the mixture was heated and refluxed on a hot water bath for 1 hour. Then excess thionyl chloride was distilled off first under atomospheric pressure and then under reduced pressure by means of an aspirator. Then, 100 ml of benzene was added to the residue and distillation under reduced pressure by the aspirator was repeated three times to remove dissolved thionyl chloride. Then, 200 ml of methanol was gradually added dropwise to the residue while cooling it. After completion of the dropwise addition, the temperature was gradually elevated and reflux under heating was conducted for 1 hour. Then, methanol was distilled off and the residue was fractionated. A fraction boiling at 78° to 80°C under 2 mm Hg was collected to obtain 45 g of 2-endo-methoxycarbonyl-2,3-exo-trimethylenenorbornane.

$n_D^{26.2}$:

1.4857 ($n_D^{20}$ of 1.4883 as taught in the reference)

Elementary Analysis Values as $C_{12}H_{18}O_2$: Found: C, 73.8; H, 9.4. Calculated: C, 74.19; H, 9.34%.

Then, a fraction boiling at 87° to 89°C under 2 mm Hg was collected to obtain 34 g of 2-exo-methoxycarbonyl-2,3-endo-trimethylenenorbornane.

$n_D^{26.5}$:

1.4911 ($n_D^{20}$ of 1.4947 as taught in the reference)

Elementary Analysis Values as $C_{12}H_{18}O_2$: Found: C 74.0: H, 9.5. Calculated: C, 74.19; H, 9.34%.

PREPARATION 3 a. Synthesis of 2-endo-hydroxymethyl-2,3-exo-trimethyleneorbornane (II) by reduction with lithium aluminum hydride:

A round-bottom flask of a capacity of 1 liter was charged with 9.83 g (0.26 mole) of lithium aluminum hydride and 400 ml of diethyl ether, and a solution of 50.25 g (0.26 mole) of 2-endo-methoxycarbonyl-2,3exo-trimethylenenorbornane obtained in Preparation 2 in 30 ml of diethyl ether was added dropwise to the charge of the flask over a period of 30 minutes at such a rate that gradual reflux could be maintained. After completion of the dropwise addition, the mixture was further refluxed for 1.5 hours. The reaction mixture was allowed to cool in air to ambient temperatures (18°–25°C) and 20 ml of ethyl acetate and then 35 ml of water were gradually added dropwise. The resulting precipitate was separated by filtration, and the filtrate was subjected to phase separation. The organic layer was dried with anhydrous sodium sulfate and the solvent was distilled off to obtain 38.3 g (yield = 88%) of 2-endo-hydroxymethyl-2,3-exo-trimethylenenorbornane (II).

Melting Point: 74° – 75°C.

Elementary Analysis Values as $C_{11}H_{18}O$: Found: C, 79.5; H, 10.9.

Calculated: C, 79.46; H, 10.92%.

$^1$Hnmr (CDCl$_3$ solvent: δ): 0.8 – 2.2 (complex multiplet, 16 H) 3.35 (singlet, 12 H);

ir (neat, cm$^{-1}$): 3400, 2960, 2850, 1470, 1450, 1310, 1250, 1075, 1020;

MS (m/e) (relative intensity): 148 (46), 135 (100), 119 (10), 107 (14), 97 (15), 93 (19), 91 (15), 81 (21), 79 (30), 67 (59), 41 (17).

b. Synthesis of 2-exo-hydroxymethyl-2,3-endo-trimethylenenorbornane (IIa) by reduction with lithium aluminum hydride:

In the same manner as described in (a) above, 20.7 g (yield = 83%) of (IIa) was prepared from 29.1 g of 2-exo-methoxycarbonyl-2,3-endo-trimethylenenorbornane.

Melting Point: 109° – 111°C.

Elementary Analysis Values as $C_{11}H_{18}O$: Found: C, 79.8; H, 10.7. Calculated: C, 79.46; H, 10.92%.

$^1$Hnmr (CDCl$_3$ solvent; δ): 0.8 – 2.2 (complex multiplet, 16 H) 3.35 (ABq, J = 10 Hz, 2H).

MS (m/e) (relative intensity): 136 (14), 135 (100), 134 (12), 93 (16), 91 (10), 81 (13), 79 (18), 77 (7), 67 (43), 41 (11).

PREPARATION 4

This Preparation describes the synthesis of 2-exo-methyl-2,3-endo-trimethylenenorbornane.

A round-bottom flask of a capacity of 500 ml was charged with 34.9 g (0.21 mole) of the alcohol obtained in Preparation 3-(b) and 100 ml of pyridine. While the charge was maintained at 20° to 25°C under cooling, 50 g (0.26 mole) of p-toluenesulfonyl chloride was added dropwise to the charge of the flask. After completion of the dropwise addition, the mixture was further stirred for 15 hours at room temperature. The reaction mixture was gradually added under cooling to 390 ml of a 15% aqueous solution of hydrochloric acid, and the resulting precipitate was recovered by filtration, washed with water and air-dried to obtain 53.6 g (yield = 79.7%) of crude 2,3-endo-trimethylenenorbornane-2-exo-methyl-p-toluenesulfonate.

Elementary Analysis Values as $C_{18}H_{24}O_3S$: Found: C, 67.4; H, 7.9; S, 9.4. Calculated: C, 67.46; H, 7.55; S, 10.00%.

1.94 g (0.051 mole) of lithium aluminum hydride and 200 ml of tetrahydrofuran were charged in a round-bottom flask of a capacity of 500 ml, and they were sufficiently stirred. Then, a solution of 16.2 g (0.051 mole) of the thus-obtained crude 2,3-endo-trimethyleneorbornane-2-exo-methyl-p-toluenesulfonate in 20 ml of tetrahydrofuran was gradually added dropwise at such a rate that gradual reflux could be maintained. After completion of the dropwise addition, the mixture was heated and refluxed for 25 hours. The reaction mixture was allowed to cool in air to room temperature (18°–25°C) and 5 ml of ethyl acetate and then 10 ml of water were gradually added dropwise. The resulting precipitate was removed by filtration, and the majority of the tetrahydrofuran was distilled off from the filtrate. The residue was subjected to phase separation, and the organic layer was recovered and fractionated. A fraction boiling at 180° to 110°C under 50 mm Hg was collected to obtain 3.57 g (yield = 46.5%) of 2-exo-methyl-2,3-endo-trimethylenenorbornane.

Melting Point: 89° – 92°C

Elementary Analysis Values as $C_{11}H_{18}$: Found: C, 87.2; H, 11.8. Calculated: C, 87.92; H, 12.08%.

$^1$Hnmr (CDCl$_3$ solvent; δ): 0.8 – 2.2 (complex multiplet); 0.99 (singlet, CH$_3$);

ir (neat, cm$^{-1}$): 2950, 2850, 1485, 1470, 1460, 1375, 1300.

MB (m/e) (relative intensity): 150 (28, M$^+$), 135 (25), 108 (79), 82 (100), 67 (96).

EXAMPLE 1

75 g of 95% sulfuric acid was added to a solution of 10 g (0.06 mole) of 2-endo-hydroxymethyl-2,3-exo-trimethylenenorbornane (II) obtained in Preparation 3-(a) in 500 ml of n-pentane, with stirring at room temperature, and the mixture was stirred for 3 hours. After the organic layer was separated, the sulfuric acid layer was extracted with 100 ml of n-pentane. The n-pentane solution was combined with the organic layer, and the mixture was washed with water, a saturated aqueous solution of sodium hydrogencarbonate and water, dried with anhydrous sodium sulfate, and fractionated.

A fraction boiling at 92° to 94°C under 14 Hg was collected to obtain 2,4exo-ethanobicyclo(3.3.1)nonane (I) in a yield of 25.5%.

Melting Point: 57°– 59°C.

Elementary Analysis Values as $C_{11}H_{18}$: Found: C, 87.5; H, 12.3. Calculated: C,87.92; H, 12.08%.

$^1$Hnmr (CDCl$_3$ solvent, δ): 0.8 – 2.4 (complex multiplet)

ir (neat, cm$^{-1}$): 3025, 2900, 2870, 1477, 1100, 982, 860, 795, 750.

MS (m/e) (relative intensity): 150 (66, M$^+$), 135 (51), 122 (95), 121 (34), 82 (35), 81 (51), 80 (73), 79 (58) 67 (100), 41 (41).

$^{13}$Cnmr (CDCl$_3$ solvent, 20Mhz, TMS at 0 ppm) (relative intensity): 18.4 (t,1), 26.5 (t,1), 28.0 (t,2), 28.4 (t,2), 31.8 (t,1), 33.2 (d,2), 41.2 (d,2.

COMPARATIVE EXAMPLE 1

10 g of 2-exo-hydroxymethyl-2,3-endo-trimethyle-nenorbornane (IIa) obtained in Preparation 3-(b) was treated under the same conditions as in Example 1 to obtain 2.7 g (yield = 30%) of 2-exo-methyl-2,3-endo-trimethylenenorbornane. The melting point, infrared absorption spectrum, $^1$Hnmr spectrum and mass spectrum were in agreement with those of the standard product obtained in Preparation 4.

The embodiments of the invention in which an exclusive property or privilege is claimed are defined as follows:

1. 2,4-exo-ethanobicyclo[3.3.1]nonane.